(12) United States Patent
Nakayama et al.

(10) Patent No.: US 6,799,472 B2
(45) Date of Patent: Oct. 5, 2004

(54) METHOD OF AND APPARATUS FOR MEASURING AND EVALUATING MATERIAL STRENGTH BY DETECTING CHARGED PARTICLES

(75) Inventors: Keiji Nakayama, Chiba-ken (JP); Kanichi Hatsukano, Ibaraki-ken (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 0 days.

(21) Appl. No.: 10/044,956

(22) Filed: Jan. 15, 2002

(65) Prior Publication Data

US 2003/0140710 A1 Jul. 31, 2003

(30) Foreign Application Priority Data

Jan. 15, 2001 (JP) ........................................ 2001-006822

(51) Int. Cl.[7] ............................................... G01N 3/08
(52) U.S. Cl. ............................... 73/827; 73/82; 702/33; 702/42
(58) Field of Search ........................... 73/81, 821, 827, 73/830, 787, 760; 702/33, 42

(56) References Cited

U.S. PATENT DOCUMENTS 4,856,326 A    8/1989    Tsukamoto
4,984,453 A    1/1991    Enomoto
5,999,887 A  * 12/1999   Giannakopoulos et al. ... 702/33
6,134,954 A  * 10/2000   Suresh et al. ................ 702/156
6,247,355 B1 *  6/2001   Suresh et al. .................. 73/82
6,311,135 B1 * 10/2001   Suresh et al. ................. 702/42

FOREIGN PATENT DOCUMENTS

JP         6-341942        12/1994

* cited by examiner

*Primary Examiner*—Edward Lefkowitz
*Assistant Examiner*—Andre Allen
(74) *Attorney, Agent, or Firm*—Oblon, Spivak, McClelland, Maier & Neustadt, P.C.

(57) ABSTRACT

A material strength measuring and evaluating method for measuring and evaluating of at least one of a peel strength and a fragility breaking strength of a fragile thin film. The method includes pressing an indenter into a test object and measuring an indentation load and an indentation depth, while at the same time detecting charged particles emitted from a peel starting point or a breakage starting point, specifying a peel occurring time and a fragility breaking time when charged particles are increased, and measuring the at least one of peel strength and the fragility breaking strength.

10 Claims, 3 Drawing Sheets

METHOD OF AND APPARATUS FOR MEASURING AND EVALUATING MATERIAL STRENGTH BY DETECTING CHARGED PARTICLES

TECHNICAL FIELD OF THE INVENTION

The present invention relates to a method of and an apparatus for measuring and evaluating the strength of a film material by measuring the peel strength of a fragile thin film. In more detail, this invention relates to a method of and an apparatus for measuring and evaluating the strength of a material, thereby measuring the peel strength as well as the fragility breaking strength of a wear resistant thin film, such as an electrically insulating thin film which might be a diamond-like carbon film useful as a protective film for protecting a magnetic recording layer of a hard disk.

DESCRIPTION OF THE RELATED ART

Since a vertical force and a tangential friction force are usually applying between the head of a hard disk and protection film on a magnetic recording layer, it is necessary to improve the fragility breaking strength against the vertical stress of the film, as well as to improve the peel strength of the film caused by the tangential force. To improve them, more precise measurement technique is required to be developed. Here, the peel strength means an interface strength between a thin film and the substrate, while the fragility breaking strength means a crack starting strength at the front end of an indenter when the indenter is vertically pressed into the film.

When measuring the peel strength of the above-described fragile film, an indenter is pressed into the surface of the film, moving downward from an upper position. Alternatively, a substrate on which a piece of film has been formed is set in an inclined position, while the indenter is pressed into an interface between the film and the substrate. The point at which a sudden and rapid change in an indentation load of the indenter happens is considered that the fragile film begins to peel from the substrate. When measuring the peel strength, a relationship between an indentation load of the indenter and an indentation displacement is obtained, thereby calculating a film peel strength in accordance with a load detected when there occurs a sudden and rapid change in the indentation load.

During a material test for evaluating a fragility breaking strength of a fragile material, an indenter is pressed into a piece of test material, thereby measuring an AE (acoustic emission) which occurs when a fragility breaking occurs, thus determining the occurrence of a breakage (for example, refer to Japanese Unexamined Patent Application Publication No. 6-341942).

However, in the above-described method by measuring an indentation displacement, there has been a problem that thee curve of a relationship between an indentation load and an indentation displacement gives is a large and unclear change, thus bringing about a considerable error in each measurement result. Moreover, with regard to the material test by measuring AE, it is required to employ a large scale apparatus for distinguishing between an AE and a noise sound.

SUMMARY OF THE INVENTION

It is an object of the present invention to provide an improved method and an improved apparatus for measuring and evaluating the strength of a material, the method and the apparatus are so formed that they can detect charged particles generated when the aforementioned film peels and a material fragility breakage occurs, thereby high-sensitively specifying a peel occurring time and a fragility breaking time, thus making it possible to correctly measure the peel strength and the fragility breaking strength.

In order to achieve the above object, the present invention provides a material strength measuring and evaluating method for measuring and evaluating a peel strength and/or a fragility breaking strength of a fragile thin film. The method comprises the steps of pressing an indenter into a test object and measuring an indentation load as well as an indentation depth, while at the same time detecting charged particles emitted from a peel starting point or a breakage starting point; specifying a peel occurring time and a fragility breaking time when charged particles are increased; measuring a peel strength and/or a fragility breaking strength.

In the above-described method, the test object may be a fragile film itself and fragile thin film covering the substrate. Further, the sample setting surface on the sample mounting base is changeable between a horizontal position and an inclined position, and the test object may be positioned horizontally while the indenter may be vertically pressed into the surface of the test object. Moreover, the test object may be arranged to form a tilt angle with the pressing direction of the indenter, so that the indenter may be pressed in a direction inclined with respect to the surface of the test object. In addition, when charged particles are collected by the charged particle collecting element, an electric potential having a polarity opposite to that of the charged particles (to be collected) is applied to the charged particle collecting element.

Furthermore, the present invention also provides a material strength measuring and evaluating apparatus for use in carrying out the aforementioned method. Such an apparatus comprises a sample mounting base for mounting a test object; an indenter to be pressed into the test object; a charged particle collecting element disposed in the vicinity of the front end portion of the indenter and formed integrally with or independently front the indenter, an indentation load detector for detecting an indentation load of the indenter; a displacement detector for detecting a displacement amount of the indenter; signal processing systems for measuring a peel strength at the time of peel occurrence and/or a fragility breaking strength at the time of fragility breaking, in accordance with the output signals fed from the indentation load detector, the displacement detector and the charged particle collecting element.

In particular, it is preferable that the front end portion of the indenter is formed by a diamond, a sapphire or a piezo-electric material. Further, it is preferable that the indentation load detector is an electronic balance positioned below the test object, while the displacement detector is a light reflection intensity meter or a light interference meter, each capable of measuring a relative displacement of the indenter with respect to the test object.

DESCRIPTION OF THE PREFERRED EMBODIMENTS

Figure 1:
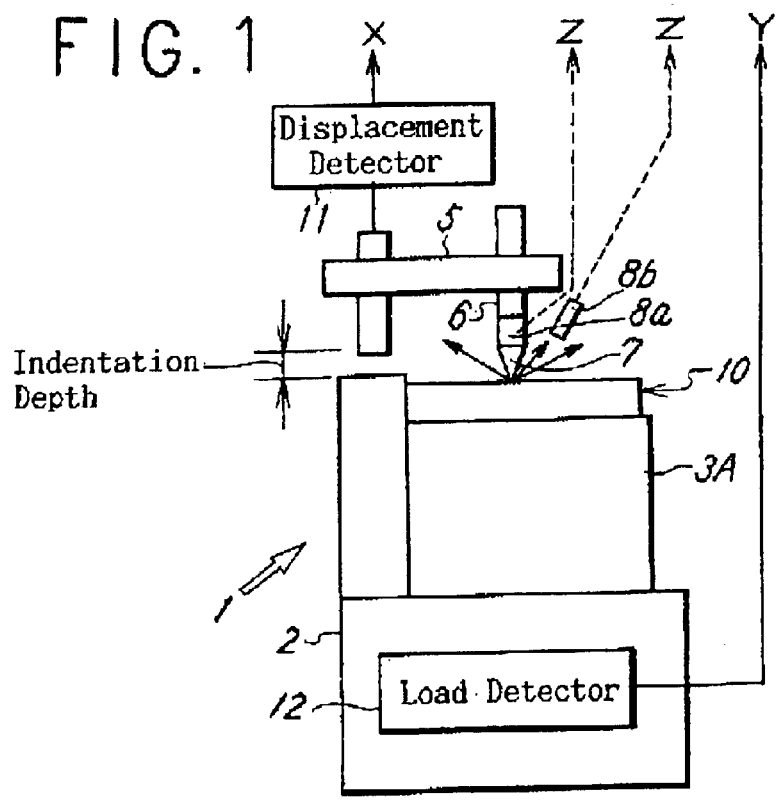
FIG. 1 to FIG. 3 are explanatory views showing several different embodiments for using the strength measurement and evaluation apparatus formed according to the present invention.
Figure 2:
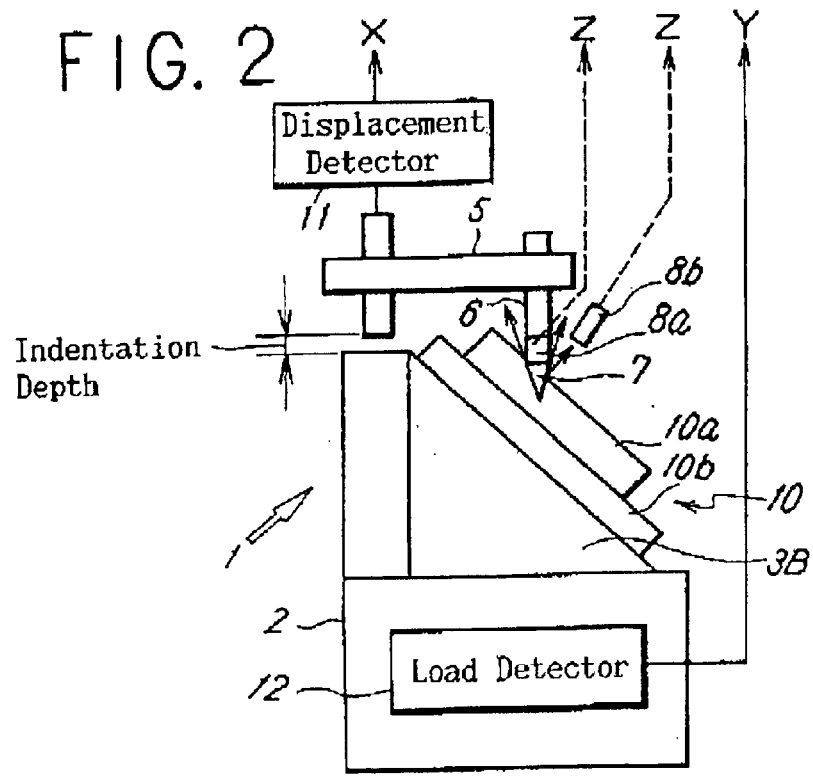
Figure 3:
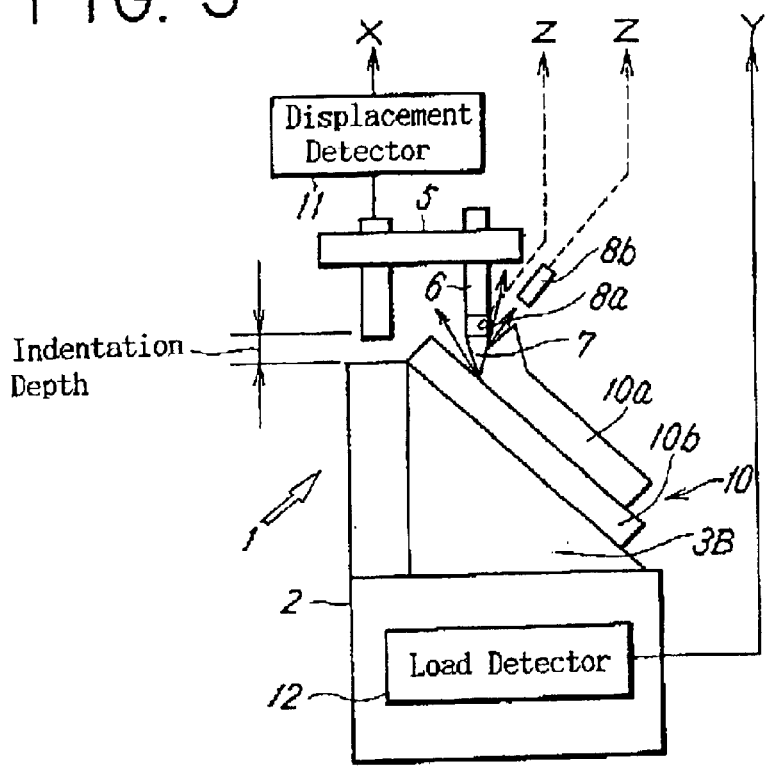

FIG. 1 to FIG. 3 are provided to show different embodiments indicating the use of the strength measurement and evaluation apparatus of the invention in carrying out the material strength measuring and evaluating method of the present invention.

As shown in FIG. 1, the strength measurement and evaluation apparatus 1 is formed by setting a sample mounting base 3A on a frame 2 in such a manner that the sample mounting base can be replaced by another one. Although the sample mounting base 3A shown in FIG. 1 indicates that its upper sample setting surface is horizontal, it is also possible to install a different sample mounting base 3B with its sample setting surface in an inclined position, as shown in FIG. 2 and FIG. 3. In fact, it is preferable that any one of the above-described sample mounting bases may be formed so that its upper sample setting surface is changeable between its horizontal position and its inclined position. Further, it is also allowed to replace the above-described changeable sample mounting bases 3A and 3B with another sample mounting base equipped with an inclination mechanism.

Specifically, FIG. 1 is used to indicate the measurement of a breaking characteristic (bulk strength) of a film material, FIG. 2 is used to indicate how to measure the peel strength on an interface between the film and its base board (substrate), and FIG. 3 is used to indicate a condition in which an indenter is pressed into an interface between the substrate and the film of a material being tested, thereby measuring a peel strength.

The frame 2 is so provided that it can hold an indenter holder 5 in a manner such that the indenter holder 5 can get close to or move away from the sample setting surface by virtue of a driving device. Specifically, the indenter holder 5 is provided to press an indenter 6 toward an object sample material located on the sample setting surface. In particular, the indenter holder 5 is so provided that it can attach thereon an indenter 6 having a sharpened front end portion 7 formed by a hard material such as a diamond, a sapphire and a piezo-electric material.

Here, in order to detect charged particles occurring at the time of peeling or fragility breaking of a film material being tested, a charged particle collecting element 8a is provided in the vicinity of the front end portion 7 of the indenter 6. In more detail, the charged particle collecting element 8a is integrally formed with the base of the front end portion 7 of the indenter 6. Alternatively, a charged particle collecting element; 8b is attached on the indenter holder 5 and is positioned in the vicinity of the front end portion 7 of the indenter 6. In this way, with the peeling and breaking of the film, positive and negative charged particles will be emitted from a peeling start point and a breaking start point. Since these positive and negative charged particles are electrons, negative ions or positive ions, if an electric voltage having a polarity opposite to that of one specific sort of the charged particles is applied to the charged particle collecting element 8a or the charged particle collecting element 8b, it is possible to collect these charged particles by virtue of the charged particle collecting element.

Furthermore, the above-described strength measurement and evaluation apparatus 1 is equipped with a displacement detector 11 for detecting a displacement of the indenter 6, while the frame 2 of the apparatus contains a load detector 12 for detecting an indentation load of the indenter 6. Moreover, although not shown in the drawings, the displacement detector 11 may be a detector of any type, provided that it allows the use of any optional device to correctly detect a relative displacement of the indenter 6 with respect to the sample mounting base during the measurement. For example, it is possible to form the displacement detector 11 by a light reflection intensity meter or a light interference meter, each capable of using a reflecting mirror provided on the sample mounting base to reflect a laser beam emitted from a laser light source attached on the indenter holder 5 and thus measuring a reflected light.

In addition, the aforesaid load detector 12 may be a detector of any type, provided that it is capable of detecting, through the indenter 6 a load exerted on the film of an object being tested. For example, it is allowed to place a precise balance on the frame 2 positioned below an object to be tested, thereby outputting a load signal of the precise balance which represents a load acting when the indenter 6 is being pressed downwardly.

Figure 4:
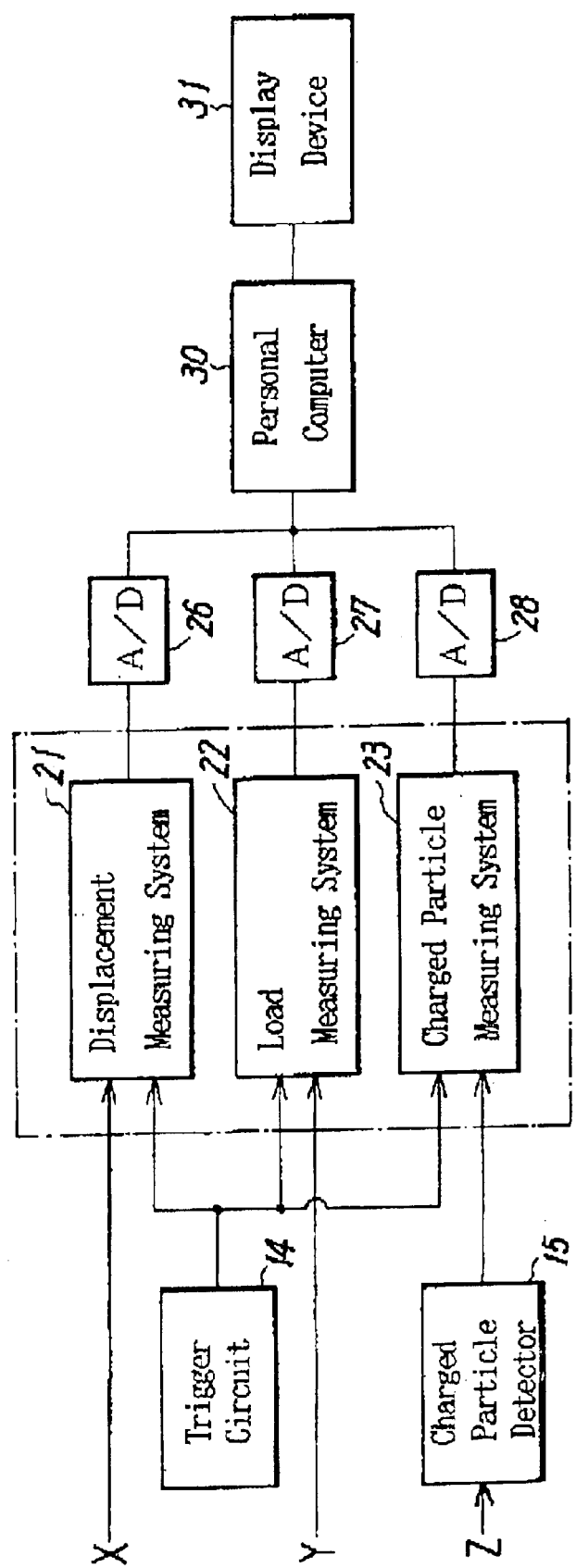
FIG. 4 is a block diagram showing several signal processing systems partly forming the aforesaid strength measurement and evaluation apparatus.

Signal processing systems shown in FIG. 4 are provided to measure the peel strength and/or fragility breaking strength upon peeling or fragility breaking, in accordance with an output of the displacement detector 11, an output of the indentation load detector 12, and an output of the charged particle collecting element 8a or 8b. In the figure, capital letters X, Y and Z are used to indicate the connection relations between the signal processing systems and the displacement detector 11, the indentation load detector 12, and the charged particle collecting elements 8a and 8b shown in FIGS. 1 to 3.

Here, the displacement detector 11 is connected with a displacement measuring system 21 shown in FIG. 4, in a manner such that the displacement measuring system 21 can operate to measure a displacement amount of the indenter in accordance with a displacement signal detected by the displacement detector 11. The load detector 12 is connected with a load measuring system 22, in a manner such that the load measuring system 22 can operate to measure an indentation load in accordance with a load signal detected by the load detector 12.

Further, the charged particle collecting element 8a or 8b is connected with a charged particle measuring system 23 through a charged particle detector 15. In fact, the Charged particle detector 15 operates to convert the electric charges collected by the charged particle collecting element 8a or 8b to an electric voltage which is then outputted to the charged particle measuring system 23. Here, the voltage, which is an output signal from the charged particle detector 15, is proportional to an electric charge amount collected, so that the charged particle measuring system 23 can perform signal amplification based on the voltage, thereby measuring a generation intensity of charged particles and a total amount of charged particle generated.

A trigger circuit 14 in connection with the displacement measuring system 21, the load measuring system 22 and the charged particle measuring system 23, is a circuit capable of providing a measurement start trigger signal to the measurement circuits of the measuring systems 21, 22 and 23. In practice, the trigger circuit 14 is comprised of an external trigger circuit and an internal trigger circuit, either of which can he selected so as to utilize the trigger circuit in a desired manner. In fact, the external trigger circuit is used to provide a voltage of several volts from the outside, thereby generating a trigger signal and thus starting a measurement. On the other hand, the internal trigger circuit operates in accordance with charged particle emission signal (voltage pulse) generated due to peeling and fragility breaking and fed from the charged particle collecting element 8a or 8b, thereby producing the trigger signal and thus starting the measurement.

Furthermore, the displacement measuring system 21, the load measuring system 22 and the charged particle measuring system 23 are all connected with a personal computer 30 through A/D converters 26, 27 and 28, thereby making it possible to record needed data in an internal memory and at the same time to output the necessary data to a display device 31 connected with the personal computer, thus displaying the output data.

Next, description will be given to explain the strength measurement and evaluation method of the present invention, which method is carried out by using the strength measurement and evaluation apparatus 1 constructed in the above-described manner.

Namely, when evaluating the breaking strength of a film material, the file material 10 is horizontally set on the sample mounting base 3A in a manner as shown in FIG. 1. On the other hand, when evaluating the peel strength of a film material, a fragile thin film 10a is formed to cover a hard substrate 10b, in a manner such that the two materials are combined together to form a test object 10, as shown in FIG. 2 and FIG. 3. Then, the test object 10 is set on a sample mounting base 3B which is in an inclined position, thereby keeping the test object in an inclined state with respect to the horizontal plane.

When a material breaking strength is evaluated in a manner shown in FIG. 1 and a material peel strength is evaluated in a manner shown in FIG. 2, the front end portion 7 of the indenter 6 is pressed into the test object 10 during measurement. Further, when the peel strength is evaluated in a manner shown in FIG. 3, the front end portion 7 of the indenter 6 is pressed into an interface between the substrate 10b and the fragile thin film 10a on the test object 10.

With the indentation movement of the indenter 6, since the positive or negative charged particles are emitted from a breaking start point or a peeling start point, the charged particles will be detected by the charged particle collecting element 8a or 8b. Meanwhile, an indentation amount (displacement amount) as well as an indentation load are respectively detected by the displacement detector 11 and the load detector 12.

Since the above-described charged particles include electrons, negative ions as well as positive ions and since these charged particles are generated when crack occurs upon the breaking of fragile solid and emitted out when an interface peel occurs between the film and its substrate, it is possible to detect, with a high sensitivity when cracking has occurred or film peeling has happened, by detecting the charged particles. Namely, a time point at which the charged particles are increased can be used to specify a time point at which the peeling has occurred or the fragility breaking has happened. At this time, a needed operation is only to measure the peel strength and/or the fragility breaking strength at such specific time.

The displacement amount and the load value detected by the displacement detector 11 and the load detector 12 are respectively measured by the displacement measuring system 21 and the load measuring system 22. On the other hand, the charged particles, upon being caught with the charged particle collecting element 8a or 8b, will be detected by the charged particle detector 15 and measured by the charged particle measuring system 23.

As described earlier in this specification, the charged particle collecting elements can have two types of collecting elements, with one being the charged particle collecting element 8a formed integrally with the indenter 6, and the other being the charged particle collecting element 8b disposed in the vicinity of the indenter and the test object. The charged particle collecting element 8a is allowed to be disposed at a position extremely close to the charged particles being generated, thereby making it possible to catch the charged particles with a high efficiency. However, it is also possible for a charged particle collecting element to be disposed in the vicinity of the indenter as well as in the vicinity of the test object, without having to be formed integrally with the indenter, just like the charged particle collecting element 8b.

When charged particles are to be caught by the charged particle collecting element 8a or 8b, if an electric potential having a different polarity from that of the charged particles (to be caught) is applied to the collecting element, it becomes possible to more effectively catch these charged particles. In other words, a negative voltage should be applied when collecting positive charged particles, while a positive voltage should be applied when collecting negative charged particles. In practice, the charged particle collecting element 8a or 8b may be formed by either a conductor or a semiconductor having a good conductivity. However, when the charged particle collecting element 8b is disposed in a vacuum condition, it is also allowed to employ a secondary electron multiplier. The signals of charged particles detected are then amplified and integrated in the charged particle measuring system 23.

In this way, the electric charge signal, the displacement signal and the load signal are simultaneously taken into process by virtue of a trigger signal fed from the common trigger circuit 14, and further fed into the personal computer 30 after being converted into digital signals in the A/D converters 26, 27 and 28. Finally, the load value and the emission intensity of the charged particles are displayed as the functions of displacement amount on the display 31.

Figure 5:
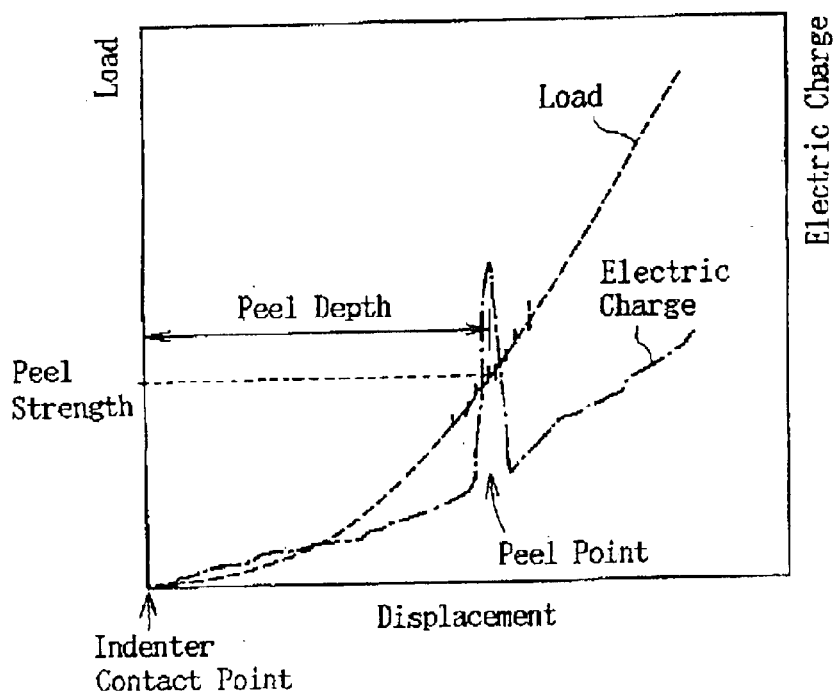
FIG. 5 is a graph showing a change in a charged particle generation amount during a peeling test conducted according to the present invention.

FIG. 5 is a graph showing a relationship between an emission amount of charged particles and an indentation load of an indenter with respect to an indenter displacement amount. In fact, such a graph is prepared under a condition where the strength measurement and evaluation apparatus 1 of the present invention is used and the test object is an alumina film formed on a glass substrate. At this time, since the indenter is in contact with the surface of the test object, and a point at which a load has been detected acts as an indenter contact point, any further displacement from that point onward will all correspond to an indentation depth formed by the indenter. With the indenter being pressed deep into the test object, charged particle emission amount will be increased due to the breaking of the alumina film. In fact, such an increase will suddenly become remarkable once the alumina film peels from the glass substrate. A load at this time may be used as a peel load.

In FIG. 5, only a slight load change can be seen when the alumina film peels from the glass substrate. Since such a load change has a relatively large range and is weak in its intensity, using such a load change makes it possible only to calculate a peel strength having a large error. In contrast to this, with the use of the present invention, it is possible to detect a peel starting point with a high sensitivity, thereby ensuring a correct calculation.

As may be clearly understood from the above description, with the use of the present invention, by detecting the charged particles generated during film peeling and material fragility breaking, it is possible to specify a peel occurring time and a fragility breaking time, with a high sensitivity as well as a high accuracy. In this way, it is possible to establish an improved method and an improved apparatus both capable of correctly measuring the peel strength and the fragility breaking strength.

What is claimed is:

1. A material strength measuring and evaluating method for measuring and evaluating at least one of a peel strength and a fragility breaking strength of a fragile thin film, said method comprising:

pressing an indenter into a test object and measuring an indentation load and an indentation depth, while at the same time detecting charged particles emitted from a peel starting point or a breakage starting point;

specifying a peel occurring time and a fragility breaking time when charged articles are increased; and measuring the at least one of peel strength and the fragility breaking strength.

2. The method according to claim 1, further comprising:
forming the test object to include a substrate and fragile thin film covering the substrate.

3. The method according to claim 1, further comprising:
horizontally positioning the test object and vertically pressing the indenter into a surface of the test object.

4. The method according to claim 1, wherein the test object is arranged to form a tilt angle with a pressing direction of the indenter, so that the indenter is pressed in a direction inclined with respect to a surface of the test object.

5. The method according to claim 1, wherein when charged particles are collected by a charged particle collecting element, an electric potential having a polarity different from that of the charged particles to be collected is applied to the charged particle collecting element.

6. A material strength measuring and evaluating apparatus, comprising:

a sample mounting base for mounting a test object;

an indenter to be pressed into the test object;

a charged particle collecting element disposed in the vicinity of a front end portion of the indenter and formed integrally with or independently from the indenter;

an indentation load detector for detecting an indentation load of the indenter;

a displacement detector for detecting a displacement amount of the indenter; and a signal processing system for measuring at least one of a peel strength at the time of peel occurrence and a fragility breaking strength at the time of fragility breaking, in accordance with output signals fed from the indentation load detector, the displacement detector and the charged particle collecting element.

7. The apparatus according claim 6, wherein a sample setting surface on the sample mounting base is changeable between a horizontal state and an inclined state.

8. The apparatus according claim 6, wherein the front end portion of the indenter is formed by a diamond, a sapphire or piezo-electric material.

9. The apparatus according claim 6, wherein the indentation load detector is an electronic balance positioned below the test object.

10. The apparatus according claim 6, wherein the displacement detector is a light reflection intensity meter or a light interference meter each for measuring a relative displacement of the indenter with respect to the test object.

* * * * *